US007897565B2

(12) United States Patent
Lin et al.

(10) Patent No.: US 7,897,565 B2
(45) Date of Patent: *Mar. 1, 2011

(54) COMPOSITIONS FOR HCV TREATMENT (75) Inventors: Kai Lin, Waltham, MA (US); Beat Weidmann, Winchester, MA (US)

(73) Assignee: Novartis AG, Basel (CH)

( * ) Notice: Subject to any disclaimer, the term of this patent is extended or adjusted under 35 U.S.C. 154(b) by 392 days.

This patent is subject to a terminal disclaimer.

(21) Appl. No.: 11/720,105

(22) PCT Filed: Dec. 20, 2005

(86) PCT No.: PCT/US2005/046059
§ 371 (c)(1),
(2), (4) Date: May 24, 2007

(87) PCT Pub. No.: WO2006/071619
PCT Pub. Date: Jul. 6, 2006

(65) Prior Publication Data
US 2009/0104149 A1 Apr. 23, 2009

Related U.S. Application Data (60) Provisional application No. 60/638,675, filed on Dec. 23, 2004.

(51) Int. Cl.
*A61K 31/7068* (2006.01)
*A61K 38/13* (2006.01)
(52) U.S. Cl. .............................................. 514/11; 514/49
(58) Field of Classification Search .................. None
See application file for complete search history.

(56) References Cited

U.S. PATENT DOCUMENTS

| 5,965,527 | A | * | 10/1999 | Barriere et al. ............... 514/11 |
| 5,994,299 | A | | 11/1999 | Jean-Christophe et al. |
| 6,524,570 | B1 | | 2/2003 | Glue et al. |
| 2002/0013272 | A1 | | 1/2002 | Cavanak et al. |
| 2002/0102279 | A1 | | 8/2002 | Chiba et al. |
| 2003/0216303 | A1 | | 11/2003 | Ambuhl et al. |

FOREIGN PATENT DOCUMENTS

| EP | 0 484 281 | 5/1992 |
| EP | 0484281 | 5/1992 |
| WO | 99/62540 | 12/1999 |
| WO | WO9962540 | 12/1999 |
| WO | 02/32447 | 4/2002 |
| WO | WO0232447 | 4/2002 |
| WO | WO 2004/002422 A2 * | 1/2004 |
| WO | 2005/021028 | 3/2005 |
| WO | WO2005/021028 | 3/2005 |
| WO | WO2006/038088 | 4/2006 |
| WO | 2006/071619 | 7/2006 |

OTHER PUBLICATIONS

Evers et al., "Synthesis of Non-immunosuppressive Cyclophilin-Binding...", Bioorganic & Medicinal Chemistry Letters, vol. 13, pp. 4415-4419, 2003.

Inque Kazuaki et al., "Combined interferon alpha2b and cyclosporin ...", Journal of Gastroenterology, vol. 38, No. 6, pp. 567-572, Jun. 2003.
Watashi K et al., "Cyclosporin A Suppresses Replication ...", Hepatology, Williams and Wilkins, Baltimore, MD, US, vol. 38, No. 5, pp. 1282-1288, Nov. 2003.
Watashi Koichi et al., "Current approaches for developing new anti-HCV agents and analyses of HCV ...", Database Biosis [Online] Biosciences Information Service, Philadelphia, PA, US, vol. 55, No. 1, pp. 105-110, Jun. 2005.
U.S. Appl. No. 10/570,097, filed Dec. 7, 2007, Makoto Hijikata, K. et al.
U.S. Appl. No. 11/719,684, filed Jan. 29, 2009, Weidmann, B.
U.S. Appl. No. 12/444,941, filed Apr. 9, 2009, Kohjima M. et al.
U.S. Appl. No. 11/572,110, filed Jan. 11, 2008, Cornu-Artis, C., et al.
Inoue et al. "Hepatitis C, virus and cyclosporin A", Igaku no Ayumi, 193(12), pp. 951-954 (2000) Included are the English abstract, the original doucment in Japanese, and an English translation of the original Japanese document.
Retrieved from: http://www3.niad.nih.gov/topics/hepatitisC/prevention.html, 2009, 2 pages [Retrieved on Jun. 27, 2009].
Inoue et al. "Antiviral effect of cyclosporin A", Antiviral Development and Therapy Poster Presentation, National Institutes of Health, Jun. 6-9, 1999.
Steinkasserer et al. "Mode of action of SDZ NIUM 811, a nonimmunosupressive cyclosporin A analog with activity against human immunodeficiency virus type 1 (HIV-1); interference with early and late events in HIV-1 replication", Journal of Virology, vol. 69, 814-824 (Feb. 1995).
Kozlowski et al., „Development of pegylated interferons for the treatment of chronic hepatitis C, BioDrugs, vol. 15, No. 7, pp. 419-429 (2001).
Hansson, 2004, Journal of Bioenergetics and Biomembranes, 36, 407-413.
Papageorgiou, 1996, Bioorganic and Medicinal Chemistry Letters, 6, 23-26.
Billich A et al. "Mode of Action SDZ NIM 811, a Nonimmunosuppressive Cyclosporin Å analog with Activity against Human Immunodeficiency Virus (HIV) Type 1: Interference with HIV Protein-Cyclophilin A Interactions", Journal of Virology, vol. 69, No. 4, pp. 2451-2461 (1995).
Yoshiba et al. "Interferon and cyclosporin A in the treatment of fulminant viral hepatitis", Journal of Gastroenterology, 30:67-73 (1995).
Renken, J., Observations under Article 115 EPC,Hoffmann Eitle, Jun. 22, 2007, pp. 2-7.
EPO, Third Party Observations Under Article 115 EPC, EP 04 764 762.3 (WO 2005/021028) Novartis, Feb. 19, 2007, pp. 1-4.
EPO, Observations by third party pursuant to Art. 115 EPC, Art. 54 EPC, Art. 56 EPC, ART 123(2) EPC, Art. 83 EPC, Art 84 EP, Feb. 8, 2007, pp. 1-6.
Watashi, Koichi et al. "Current approaches for developing new anti-HCV agents and analyses of HCV replication using anti-HCV agents", Biosis, Biosciences Information Service, Philadelphia, PA, US; vol. 55, No. 1, pp. 105-110, Jun. 2005.

(Continued)

*Primary Examiner* — Jeffrey E Russel
(74) *Attorney, Agent, or Firm* — Leslie Fischer (57) ABSTRACT

The present invention concerns a pharmaceutical combination comprising a) a first agent which is a non-immunosuppressive cyclophilin-binding cyclosporine, e.g., a compound of formula I and b) a co-agent. Co-agents include, but are not limited to, interferons, a conjugate of interferon, antiviral agents, helicase inhibitors, protease inhibitors, polymerase inhibitors and nucleoside analogs. The instant pharmaceutical combination may be used, e.g., in treating subjects having a flaviviridae infection, e.g., a Hepatitis C infection.

12 Claims, 3 Drawing Sheets

OTHER PUBLICATIONS

Duncan and Youossi (2003), Cleveland Clinic, J. Med., 70:S21-S26.

Shiffman (2004), Cleveland Clinic, J. Med., 71:S13-S16.

Agid et al., "MR diffusion-weighted imaging in a case of West Nile virus encephalitis", Dec. 23, 2003, Neurology. vol. 61., No. 12, pp. 1821-1823.

Ravindra, K. V. et al., "West Nile virus-associated encephalitis in recipients of renal and pancreas transplants . . . ", May 1, 2004, Clinical Infectious Diseases, vol. 38, No. 9, pp. 1257-1260.

Quesniaux, V. F. J. et al, "Cyclophilin binds to the region of cyclosporine involved in its immunosuppressive . . . ", 1987, European Journal of Immunology, vol. 17, No. 9, pp. 1359-1365.

Papatheodoridis and Cholongitas (2003), J. Viral Hep., 11:287-296.

Tripi, et al., "Interferon-alpha Alone versus interferon-alpha plus Ribavirin in Patients with Chronic Hepatitis C Not Responding to Pervious Interferon-alpha treatment.", BioDrugs, vol. 13, No. 4, pp. 229-304 (Apr. 2000).

Brown, et al., "Liver Transportation", Current opinion gastroenterology, vol. 17, No. 3, pp. 299-303 (May 2001).

Ferenci, P., International Journal Of Clinical Practice, vol. 57, No. 7, pp. 610-615, "Peginterferon alfa-2a (40KD) (Pegasys) for the treatment of patients with chronic hepatitis C", Sep. 7, 2003.

Manns, M.P., et al., The Lancet, vol. 358, No. 9286, pp. 958-964, "Peginterferon alfa-2b plus ribavirin compared with interferon alfa-2b plus ribavirin for initial treatment of chronic hepatitis C: a randomised trial", Aug. 2001.

Manzarbeitia, C., et al., "40 kDa Peginterferon alfa-2A (PEGASYSs®) as a prophylaxis against hepatitis C infection recurrence after liver transplantation (LT); preliminary results of a randomized multicenter trial", p. 406A, AbstractsAASLD No. 938, Hepatology, Oct. 2001.

Nakagawa, M., et al., Biochemical and Biophysical Research Communications, Academic Press Inc., Orlando, FL, vol. 313, No. 1, pp. 42-47, "Specific inhibition of hepatitis C virus replication by cyclosporin A", Jan. 2, 2004.

International Search Report and written opinion for PCT/EP2005/007633, dated Oct. 19, 2005.

Bizollon T. et al., "Histological Benefit of Retreatment by Pegylated Interferon Alfa-2b and Ribavirin in Patients with Recurrent Hepatitis C Virus Infection Posttransplantation", American Journal of Transplantation, vol. 7, pp. 448-453, (2007).

Cotler, Scott J. et al., "A Pilot Study of the Combination of Cyclosporin A and Interferon Alfacon-1 for the Treatment of Hepatitis C in Previous Nonresponder Patients", J Clin Gastroenterol, vol. 36 (4), pp. 352-355, (2003).

Dasilva, et al. (2002) J. Gastroenterol 37:732-36F.

Heathcote, et al. (1998) Hepatology 27:4, pp. 1136-1143.

Package Insert for Intron A, Revision Jul. 2007.

Fukushima et al., "Fasudil hydrochloride hydrate, a rhokinase (ROCK) inhibitor, suppresses collagen production and enhances collagenase activity in hepatic stellate cells", 2005,Liver International, vol. 25, pp. 829-838.

Fukushima et al., "Hydroxyfasudil, a Rho-kinase (ROCK) inhibitor suppresses cell growth and collagen production in rat hepatic stellate cells", 2003, Hepatology, vol. 38, No. 4, Suppl. 1, p. 562A.

Nakamuta et al., "Cyclosporine suppresses cell growth and collagen production in hepatic stellate cells", 2005, Transplantation Proceedings, vol. 37, No. 10.

Inoue et al., "Combined interferon A2b and cyclosporine A in the treatment of chronic hepatitis C: controlled trial", Journal of Gastroenterol, vol. 38, No. 6, pp. 567-572, , Jun. 2003.

Inoue. 2001, Nippon Rinsho (translation enclosed) (referred further as 'Inoue (Nippon)'), in view of Bouchard, 2003, Journal of Virology, 77, 7713-7719 in view of Bartz, 1995, PNAS, 92, 5381-5385.

Bouchard, 2003, Journal of Virology, 77, 7713-7719.

Bartz, 1995, PNAS, 92, 5381-5385.

Office Action mailed from USPTO Dec. 15, 2009, U.S. Appl. No. 10/570,097.

Inoue K., et al; "Combined Interferon a2b and Cyclsporin A in the treatment of chronic hepatitis C: controlled trial"; J. Gastroenterology, vol. 38, pp. 567-572 (2003).

Inoue, K., et al; "IFN/CsA Therapy", Nippon Rinsho, vol. 59, No. 7, pp. 1326-1330 (2001).

Bouchard, M. et al; "Activation and Inhibition of Cellular Calcium and Tyrosine Kinase Signaling Pathways Identify Targets of the HBx Protein Involved in Hepatitis B Virus Replication", J. Virology, vol. 77, No. 14, pp. 7713-7719 (2003).

Bartz, S., et al, "Inhibition of Human Immunodeficiency virus replication by non immunosuppressive analogs of cyclosporin A", vol. 92, pp. 5381-5385 (1995).

* cited by examiner

SEQUENCE LISTING

<160> NUMBER OF SEQ ID NOS: 3

<210> SEQ ID NO 1
<211> LENGTH: 21
<212> TYPE: DNA

```
<213> ORGANISM: Artificial
<220> FEATURE:
<223> OTHER INFORMATION: HCV-specific primer

<400> SEQUENCE: 1
tcttcacgca gaaagcgtct a                                      21

<210> SEQ ID NO 2
<211> LENGTH: 19
<212> TYPE: DNA
<213> ORGANISM: Artificial
<220> FEATURE:
<223> OTHER INFORMATION: HCV-specific primer

<400> SEQUENCE: 2
ctggcaattc cggtgtact                                         19

<210> SEQ ID NO 3
<211> LENGTH: 25
<212> TYPE: DNA
<213> ORGANISM: Artificial
<220> FEATURE:
<223> OTHER INFORMATION: HCV-specific probe

<400> SEQUENCE: 3
tcctggaggc tgcacgacac tcata                                  25
```

COMPOSITIONS FOR HCV TREATMENT

This application is the National Stage of Application No. PCT/US05/046059, filed on Dec. 20, 2005 which claims benefit under 35 U.S.C. §119(e) of U.S. Provisional Application No. 60/638,675, filed Dec. 23, 2004, the contents of which are incorporated herein by reference in their entirety.

FIELD OF THE INVENTION

The invention is directed to the area of pharmaceutical chemistry, in particular to nonimmunossuppressive cyclosporins and combination treatment of Hepatitis C infection.

BACKGROUND OF THE INVENTION

The present invention relates to a new use for non-immunosuppressive cyclosporins. The cyclosporins comprise a class of structurally distinctive, cyclic, poly-N-methylated undecapeptides, commonly possessing pharmacological, in particular immunosuppressive, or anti-inflammatory activity. The first of the cyclosporins to be isolated was the naturally occurring fungal metabolite Ciclosporin or Cyclosporine, also known as cyclosporin A.

It is well established that cyclosporin A acts by interfering with the process of T cell activation by blocking transcription initiation of IL-2. Cyclosporin A has been shown to form a complex with a 17 kD cytosolic protein named as cyclophilin, that occurs in many cell types and has been shown to be identical to peptidyl-prolyl cis-trans isomerase, an enzyme involved in protein folding.

However, it was found that binding to cyclophilin is a necessary but not a sufficient criterion for immunosuppressive activity. The cyclosporin A/cyclophilin complex can also associate with the cellular protein named calcineurin (CN) which belongs to the phosphatase superfamiliy. This binding abrogates its phosphatase activity, resulting in silencing of transcription factor NF-AT. The inhibition of the CN/NF-AT pathway is the essential mechanism for cyclosporin A mediated immunosuppression.

Cyclosporins which bind strongly to cyclophilin but are not immunosuppressive have been identified. A cyclosporin is considered to be non-immunosuppressive when it has an activity in the Mixed Lymphocyte Reaction (MLR) of no more than 5%, preferably no more than 2%, that of cyclosporin A. The Mixed Lymphocyte Reaction is described by T. Meo in "Immunological Methods", L. Lefkovits and B. Peris, Eds., Academic Press, N.Y. pp. 227-239 (1979). Spleen cells ($0.5 \times 10^6$) from Balb/c mice (female, 8~10 weeks) are co-incubated for 5 days with $0.5 \times 10^6$ irradiated (2000 rads) or mitomycin C treated spleen cells from CBA mice (female, 8~10 weeks). The irradiated allogeneic cells induce a proliferative response in the Balb/c spleen cells which can be measured by labeled precursor incorporation into the DNA. Since the stimulator cells are irradiated (or mitomycin C treated) they do not respond to the Balb/c cells with proliferation but do retain their antigenicity. The $IC_{50}$ found for the test compound in the MLR is compared with that found for cyclosporin A in a parallel experiment. In addition, non-immunosuppressive cyclosporins lack the capacity of inhibiting CN and the downstream NF-AT pathway.

EP 0 484 281 A1 discloses the use of non-immunosuppressive cyclosporins in the treatment of AIDS or AIDS-related disorders. As disclosed in application EP 2004/009804, non-immunosuppressive cyclosporins which bind to cyclophilin have also been found to have an inhibitory effect on Hepatitis C virus (HCV).

SUMMARY OF THE INVENTION

It has been discovered that a non-immunosuppressive cyclosporin provides superior results against flaviviridae, specifically, a hepatitis C virus. Based on this discovery, compositions, methods, and uses are provided for the treatment of hepatitis C infections, that include administration of an effective amount of a non-immunosuppressive cyclosporin in combination with one or more co-agents, salts, esters, prodrugs or derivatives thereof.

DETAILED DESCRIPTION

All disclosures referenced herein are incorporated by reference in their entirety.

It has now surprisingly been found that non-immunosuppressive cyclosporins which bind to cyclophilin have an inhibitory effect on hepatitis C virus (HCV) and that when used in combination with other anti-viral pharmaceutical agents, such combinations are particularly effective.

Persistent infection by HCV, which has been identified as the major causative agent of non-A, non-B hepatitis has been considered closely related to liver diseases such as chronic hepatitis, liver cirrhosis or hepatocellular carcinoma. The development of these liver diseases is a major public health problem. Effective anti-HCV therapy is restricted to therapy with interferon alpha or a combination of interferon alpha and ribavirin. However, since the virus is not eliminated from about a half of the HCV patients treated with these known agents, there is still a strong need for alternative anti-HCV treatments.

Accordingly, the present invention provides the use of a non-immunosuppressive cyclophilin-binding cyclosporin in the prevention or treatment of hepatitis C or HCV induced disorders when used in combination with other therapeutic agents. Hepatitis C or HCV induced disorders are e.g. chronic hepatitis, liver cirrhosis or liver cancer, e.g. hepatocellular carcinoma. The non-immunosuppressive cyclophilin-binding cyclosporin and its combination with other therapeutic agents may also be used for example as a prophylactic treatment of neonates born to HCV infected mothers or of healthcare workers exposed to the virus, or of transplant recipients, e.g. liver transplant recipients, to eliminate possible recurrent HCV infection after transplantation.

A cyclosporin is considered as binding to cyclophilin if it binds to human recombinant cyclophilin at least one fifth as well as does cyclosporin A in the competitive ELISA test described by Quesniaux in Eur. J. Immunol. 1987 17:1359-1365. In this test, the cyclosporin to be tested is added during the incubation of cyclophilin with coated BSA-cyclosporin A and the concentration required to give a 50% inhibition of the control reaction without competitor is calculated ($IC_{50}$). The results are expressed as the Binding Ratio (BR), which is the log to the base 10 of the ratio of the $IC_{50}$ of the test compound and the $IC_{50}$ in a simultaneous test of cyclosporin A itself. Thus a BR of 1.0 indicates that the test compound binds human cyclophilin one factor of ten less well than does cyclosporin A, and a negative value indicates binding stronger than that of cyclosporin A. The cyclosporins active against HCV have a BR lower than 0.7, such as equal to or lower than zero.

Examples of non immunosuppressive cyclophilin-binding cyclosporins include e.g. compounds of Formula I in which
W is MeBmt, dihydro-MeBmt or 8'-hydroxy-MeBmt;
X is αAbu, Val, Thr, Nva or 0-methyl threonine (MeOThr);
R is Sar, (D)-MeSer, (D)-MeAla, or (D)-MeSer(Oacetyl);
Y is MeLeu, γ-hydroxy-MeLeu, MeIle, MeVal, MeThr, MeAla,
   MeaIle or MeaThr; N-ethylVal, N-ethylIle, N-ethylThr, N-ethylPhe, N-ethylTyr or N-ethylThr(Oacetyl)
Z is Val, Leu, MeVal or MeLeu; and
Q is MeLeu, γ-hydroxy-MeLeu or MeAla.

The groups W, X, Y, Z, Q and R have, independently, the following preferred significances:
W is preferably W' where W' is MeBmt or dihydro-MeBmt;
X is preferably X' where X' is αAbu or Nva, more preferably X" where X" is αAbu;
R is preferably R' where R' is Sar;
Y is preferably Y' where Y' is γ-hydroxy-MeLeu, MeVal, MeThr, MeIle, N-ethylIle or N-ethylVal;
Z is preferably Z' where Z' is Val or MeVal; and
Q is preferably Q' where Q' is MeLeu;

A preferred group of Compounds of formula I are those in which W is W', X is X', Y is Y', Z is Z', Q is Q' and R is R'.
Examples of preferred compounds of Formula I are e.g.:
a) [dihydro-MeBmt]$^1$-[γ-hydroxy-MeLeu]$^4$-Ciclosporin; BR*=0.1; IR<1%
b) [MeVal]$^4$-Ciclosporin; BR=0.1; IR<1%
c) [MeIle]$^4$-Ciclosporin; BR=−0.2; IR<1%
d) [MeThr]$^4$-Ciclosporin;
e) [γ-hydroxy-MeLeu]$^4$-Ciclosporin; BR=0.4; IR<1%
f) [Ethyl-Ile]$^4$-Ciclosporin; BR=0.1; IR<2%
g) [Ethyl-Val]$^4$-Ciclosporin; BR=0; IR<2%
h) [Nva]$^2$-[γ-hydroxy-MeLeu]$^4$-Ciclosporin;
i) [γ-hydroxy-MeLeu]$^4$-[γ-hydroxy-MeLeu]$^6$-Ciclosporin;
j) [MeVal]$^5$-Ciclosporin; BR=0.4; IR=5.3%
k) [MeoThr]$^2$-[(D)MeAla]$^3$-[MeVal]$^5$-Ciclosporin;
j) [8'-hydroxy-MeBmt]$^5$-Ciclosporin; BR=0.35; IR=1.8%
k) [MeAla]$^6$-Ciclosporin; BR=−0.4; IR=3.2
l) [γ-hydroxy-MeLeu]$^9$-Ciclosporin; BR=0.15; IR=2.9

IR=Immunosuppressive Ratio, expressed as a percentage of the activity relative to Cyclosporin A.

Further examples of non-immunosuppressive cyclosporins are the compounds disclosed in WO 98/28330, WO 98/28329 and WO 98/28328, the contents thereof being incorporated herein by reference, e.g. compounds of formula II wherein
$W_a$ is wherein $R_a$ is a residue of formula Ic or Id in which $R_4$ is $C_{1-4}$alkylthio, amino$C_{1-4}$alkylthio, $C_{1-4}$alkylamino$C_{1-4}$alkylthio, di$C_{1-4}$alkylamino-$C_{1-4}$alkylthio, pyrimidinylthio, thiazolylthio, N—$C_{1-4}$alkylimidazolylthio, hydroxy$C_{1-4}$alkylphenylthio, hydroxy$C_{1-4}$alkylphenoxy, nitrophenylamino or 2-oxopyrimidin-1-yl, and $R_{14}$ is $C_{1-4}$alkyl,
$X_a$ is Abu;
$R_1$ is —NMe-CH($R_b$)—CO— wherein $R_b$ is H or —S-Alk-$R_0$ in which Alk-$R_0$ is methyl; or Alk is straight or branched $C_{2-6}$alkylene or $C_{3-6}$cycloalkylene and $R_0$ is H; OH; COOH; $C_{2-5}$alkoxy-carbonyl; $NR_1R_2$ in which each of $R_1$ and $R_2$, independently, is selected from H, $C_{1-4}$alkyl, $C_{2-4}$alkenyl, $C_{3-6}$cycloalkyl and phenyl each optionally substituted by halogen, $C_{1-4}$alkoxy, $C_{2-5}$alkoxycarbonyl, amino, $C_{1-4}$alkylamino and/or di$C_{1-4}$alkyl-amino, and benzyl and a heterocyclic radical, said benzyl and heterocyclic radicals being saturated or unsaturated and containing 5 or 6 ring members and 1 to 3 heteroatoms, or $R_1$ and $R_2$ form, together with the nitrogen atom to which they are attached, a 4- to 6 membered heterocycle which may contain another heteroatom chosen from nitrogen, oxygen and sulphur, and which is optionally substituted by $C_{1-4}$alkyl, phenyl or benzyl; or each of $R_1$ and $R_2$, independently, is a radical of formula Ib in which $R_1$ and $R_2$ are as defined above, $R_3$ is H or $C_{1-4}$alkyl and n is an integer ranging from 2 to 4;
$Y_a$ is MeLeu or γ-hydroxy-MeLeu;
$Z_a$ is Val; and
$Q_a$ is MeLeu,
with the proviso that $R_b$ is not H when $Y_a$ is MeLeu, or a pharmaceutically acceptable salt thereof.

In the formula II, when $R_1$, and/or $R_2$ is a heterocyclic residue, it may be pyridyl, tetrahydro-pyridyl, piperidyl, imidazolyl, oxazolyl or thiazolyl. When $R_1$ and $R_2$ form a heterocyclic residue with the nitrogen atom to which they are attached, by way of example, the heterocyclic residue may be chosen from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl (for example 4-methyltetrahydropyridyl) or phenyltetrahydropyridyl (for example 4-phenyltetrahydropyridyl).

The Compounds of formula I, Ia or II may be obtained in a variety of ways, which may be classified as:
1) Fermentation
2) Biotransformation
3) Derivatisation
4) Partial Synthesis
5) Total Synthesis as disclosed e.g. in EP 0 484 281 A1, WO 00/01715, WO 98/28330, WO 98/28329 or WO 98/28328 the contents thereof being incorporated herein by reference.

In a series of further specific or alternative embodiments, the present invention also provides:

1.1 A method for preventing or treating Hepatitis C infections or HCV induced disorders in a subject in need thereof, comprising administering to said subject the combination of a therapeutically effective amount of a non-immunosuppressive cyclophilin-binding cyclosporin, e.g. a compound of formula I, in combination with one or more co-agents 1.2 A method for inhibiting HCV replication in a medium, comprising applying to this medium an effective amount of a non-immunosuppressive cyclophilin-binding cyclosporin, e.g. a compound of formula I, in combination with one or more co-agents 1.3 A method for inhibiting HCV replication in a patient in need thereof, comprising administering to this subject a therapeutically effective amount of a non-immunosuppressive cyclophilin-binding cyclosporin, e.g. a compound of formula I, in combination with one or more co-agents.

1.4 A method for preventing the recurrence of HCV infection in a transplant recipient in need thereof, comprising administering to said recipient a therapeutically effective amount of a non-immunosuppressive cyclophilin-binding cyclosporin, e.g. a compound of formula I, in combination with one or more co-agents.

2. Use of the combination of a non-immunosuppressive cyclophilin-binding cyclosporine, e.g. a compound of formula I, with one or more co-agents in the preparation of a pharmaceutical composition for use in any method as defined above.

3. A pharmaceutical composition for use in any method as defined above, comprising a non-immunosuppressive cyclophilin-binding cyclosporin, e.g. a compound of formula I, in combination with one or more co-agents, and together with one or more pharmaceutically acceptable diluents or carriers thereof.

In another aspect, suitable co-agents that can be used in combination or alternation treatment include but are not limited to:

(1) Interferons or conjugates of interferons such as:
   (a) Intron-A®, interferon alfa-2b (Schering Corporation, Kenilworth, N.J.),
   (b) PEG-Intron®, peginteferon alfa-2b (Schering Corporation, Kenilworth, N.J.),
   (c) Roferon®, recombinant interferon alfa-2a (Hoffmann-La Roche, Nutley, N.J.),
   (d) Pegasys®, peginterferon alfa-2a (Hoffmann-La Roche, Nutley, N.J.),
   (e) Berefor®, interferon alfa 2 available (Boehringer Ingelheim Pharmaceutical, Inc., Ridgefield, Conn.),
   (f) Sumiferon®, a purified blend of natural alpha interferons (Sumitomo, Japan),
   (g) Wellferon®, lymphoblastoid interferon alpha n1 (GlaxoSmithKline),
   (h) Infergen®, consensus alpha interferon (InterMune Pharmaceuticals, Inc., Brisbane, Calif. and Amgen, Inc., Newbury Park, Calif.),
   (i) Alferon®, a mixture of natural alpha interferons (Interferon Sciences, and Purdue Frederick Co., CT),
   (j) Viraferon®;
   (k) Conjugated interferons include, for example, Albuferon (Human Genome Science)

which is conjugated to human albumin. Interferon conjugated to a water-soluble polymer or polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Interferon-polymer conjugates are described in U.S. Pat. No. 4,766,106, U.S. Pat. No. 4,917,888, EPA 0 236 987, EPA 0 510 356 and WO 95/13090. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced.

Other forms of interferons include interferon beta, gamma, tau and omega, such as Rebif (Interferon beta 1a) by Serono, Omniferon (natural interferon) by Viragen, or Omega Interferon by Boehringer Ingelheim;

Oral interferons such as oral interferon alpha by Amarillo Biosciences;

In another aspect, additional examples of interferons include pegylated interferon alpha, for example pegylated interferon α-2a, pegylated interferon α-2b, pegylated consensus interferon or pegylated purified interferon-α product. Pegylated interferon α-2a is described in European Patent 593,868 (incorporated herein by reference in its entirety) and commercially available e.g. under the trade name PEGASYS® (Hoffmann-La Roche). Pegylated interferon-α-2b is described, e.g. in European Patent 975,369 (incorporated herein by reference in its entirety) and commercially available e.g. under the trade name PEG-INTRON A® (Schering Plough). Pegylated consensus interferon is described in WO 96/11953 (incorporated herein by reference in its entirety).

(2) Antivirals

Antiviral agents may be compounds or biologicals that are effective to inhibit the formation and/or replication of a virus in a mammal. This includes agents that interfere with either host or viral mechanisms necessary for the formation and/or replication of a virus in a mammal such as ribavirin (1-beta-D-ribofuranosyl-1H-1,2,4-triazole-3-carboxamide) from Valeant Pharmaceuticals, Inc., Costa Mesa, Calif., Rebetol® from Schering-Plough Corporation, Kenilworth, N.J., and Copegus® from Hoffmann-La Roche, Nutley, N.J., ribavirin analogues in development such as Levovirin and Viramidine by Valeant, and Mizoribine Monophosphate;

(3) Protease Inhibitors

Inhibitors of HCV NS3-4A serine protease such as substrate-based protease inhibitors (Attwood et al., *Antiviral peptide derivatives*, PCT WO 98/22496, 1998; Attwood et al., Antiviral Chemistry and Chemotherapy 1999, 10, 259-273; Attwood et al, Preparation and use of amino acid derivatives as anti-viral agents, German Patent Pub. DE 19914474; Tung et al. Inhibitors of serine proteases, particularly hepatitis C virus NS3 protease; PCT WO 98/17679), including alphaketoamides and hydrazinoureas, and inhibitors that terminate in an electrophile such as a boronic acid or phosphonate (Llinas-Brunet et al. Hepatitis C inhibitor peptide analogues, PCT WO 99/07734);

Protease inhibitors disclosed in U.S. patents for the treatment of HCV, for example, U.S. Pat. No. 6,004,933 to Spruce et al which discloses a class of cysteine protease inhibitors for inhibiting HCV endopeptidase 2; U.S. Pat. No. 5,990,276 to Zhang et al which discloses synthetic inhibitors of hepatitis C virus NS3 protease; U.S. Pat. No. 5,538,865 to Reyes et al.; Peptides as NS3 serine protease inhibitors of HCV which are disclosed in WO 02/008251 to Corvas International, Inc., and WO 02/08187 and WO 02/008256 to Schering Corporation HCV inhibitor tripeptides which are disclosed in U.S. Pat. Nos. 6,534,523, 6,410,531 and 6,420,380 to Boehringer Ingelheim and WO 02/060926 to Bristol Myers Squibb (incorporated herein by reference in their entireties); Diaryl peptides as NS3 serine protease inhibitors of HCV which are disclosed in WO 02/48172 to Schering Corporation; Imidazoleidinones as NS3 serine protease inhibitors of HCV which are disclosed in WO 02/18198 to Schering Corporation and WO 02/48157 to Bristol Myers Squibb (incorporated herein by reference in their entireties); WO 98/17679 to Vertex Pharmaceuticals and WO 02/48116 to Bristol Myers Squibb also disclose HCV protease inhibitors (incorporated herein by reference in their entireties).

(4) Non-substrate-based NS3 protease inhibitors such as 2,4,6-trihydroxy-3-nitro-benzamide derivatives (Sudo K. et al., *Biochemiscal and Biophysical Research Communications*, 1997, 238 643-647; Sudo K. et al. *Antiviral Chemistry and Chemotherapy*, 1998, 9, 186), including RD3-4082 and RD3-4078;

(5) A phenanthrenequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), (Chu M et al., *Tetrahedron Letters* 37:7229-7232, 1996); Sch 351633, isolated from the fungus *Penicillium grieofulvum* (Chu M. et al., *Bioorganic and Medicinal Chemistry Letters* 9:1949-1952); selective inhibitors designed based on the macromolecule eglin c., which is isolated from leech and is a potent inhibitor of several serine proteases such as *S. griseus* proteases A and B, ∀-chymotrypsin, chymase and subtilisin (Qasim M. A. et al., *Biochemistry* 36:1598-1607, 1997).

(6) Thiazolidines and benzanilides identified in Kakiuchi N. et al. *J. FEBS Letters* 421, 217-220; Takeshita N. et al. *Analytical Biochemistry*, 1997, 247, 242-246. Thiazolidine derivatives which show relevant inhibition in a reverse-phase HPLC assay with an NS3/4A fusion protein and NS5A/5B substrate (Sudo K. et al., *Antiviral Research*, 1996, 32, 9-18). especially compound RD-16250 possessing a fused cinnamoyl moiety substituted with a long alkyl chain, RD4 6205 and RD4 6193

(7) HCV NS3-4A serine protease inhibitors including BILN 2061 by Boehringer Ingelheim, VX-950 by Vertex, SCH-6, SCH-7, and SCH-351633, by Schering-Plough, and other HCV protease inhibitors in preclinical and clinical development by GlaxoSmithKline, Bristol Myers Squibb, Abbot, Roche, Merck, Pfizer, and Gilead;

(8) Nucleoside Analogs

Telbivudine by Idenix (U.S. Pat. No. 6,444,652, U.S. Pat. No. 6,596,700, and WO0196353)

Nucleoside or non-nucleoside inhibitors of HCV NS5B RNA-dependent RNA polymerase, such as 2'-C-methyl-3'-O-L-valine ester ribofuranosyl cytidine (NM283, Idenix) as disclosed in WO 2004/002422.

Branched nucleosides disclosed by Idenix Pharmaceuticals for the use of treatment of flaviviruses (including HCV) and pestiviruses in International Publication Nos. WO 01/90121 and WO 01/92282 (incorporated herein by reference in their entireties). Specifically, a method for the treatment of hepatitis C infection (and flaviviruses and pestiviruses) in humans and other host animals is disclosed in the Idenix publications that includes administering an effective amount of a biologically active 1', 2', 3' or 4'-branced B-D or B-L nucleosides or a pharmaceutically acceptable salt or prodrug thereof, administered either alone or in combination with another antiviral agent, optionally in a pharmaceutically acceptable carrier.

Nucleoside analogs in other patent applications disclosing the use of treatment of hepatitis C virus include: PCTCA00/01316 (WO 01/32153; filed Nov. 3, 2000) and PCT/CA01/00197 (WO 01/60315; filed Feb. 19, 2001) filed by BioChem Pharma, Inc., (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd. (the disclosures of which are incorporated herein by reference in their entireties)

2'-fluoronucleosides disclosed in PCT Publication No. WO 99/43691 to Emory University (incorporated herein by reference in its entirety), entitled "2'-Fluoronucleosides";

2'-modified nucleosides disclosed by Eldrup et al. (Oral Session V, Hepatitis C Virus, Flaviviridae; 16$^{th}$ International Conference on Antiviral Research (Apr. 27, 2003, Savannah, Ga.));

Nucleoside analogues and 2'-modified nucleosides disclosed in Bhat et al. (Oral Session V, Hepatitis C Virus, Flaviviridae, 2003 (Oral Session V, Hepatitis C Virus, Flaviviridae; 16$^{th}$ International conference on Antiviral Research (Apr. 27, 2003, Savannah, Ga.); p A75);

2'-modified nucleosides disclosed in Olsen et al. (Oral Session V, Hepatitis C Virus, Flaviviridae; 16$^{th}$ International Conference on Antiviral Research (Apr. 27, 2003, Savannah, Ga.) p A76)

Preclinical compounds include R803 (Rigel), JTK-003 (Japan Tabacco), HCV-086 (ViroPharma/Wyeth), R-1479 (Roche);

(9) Nucleotide polymerase inhibitors and gliotoxin (Ferrari R. et al. *Journal of Virology*, 1999, 73, 1649-1654), and the natural product cerulenin (Loh mann V. et al. *Virology*, 1998, 249, 108-118);

(10) HCV NS3 helicase inhibitors, such as VP_50406 by ViroPhama and compounds from Vertex, other helicase inhibitors disclosed in U.S. Pat. No. 5,633,388 and PCT WO 97/36554;

(11) Antisense molecules directed against HCV genome or any cellular component that is required for viral replication.

Phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 199, 181, 251-257); such as ISIS 14803 by Isis Pharm/Elan, antisense oligonucleotides by Hybridon, AVI bioPharma and Chugai, AVI-4065 (AVI BioPharma), or an antisense sequence complementary to any part of the HCV genome which increases effectiveness of therapy;

(12) Inhibitors of IRES-dependent translation (Ikeda N et al., *Agent for the prevention and treatment of hepatitis C*, Japanese Patent Pub. JP-08268890; Kai Y et al. *Prevention and treatment of viral diseases*, Japanese Patent Pub. JP-10101591); such as ISIS 14803 by Isis Pharm/Elan, IRES inhibitors by PTC Therapeutics, Anadys, Immusol, RiboTargets, and SomaGenics;

(13) Ribozymes, such as nuclease-resistant ribozymes (Maccjak, D. J. et al., *Hepatology* 1999, 30, abstract 995) and those directed in U.S. Pat. No. 6,043,077 to Barber et al., and U.S. Pat. Nos. 5,869,253 and 5,610,054 to Draper et al. (incorporated herein by reference in their entireties) for example, HEPTAZYME by RPI, and Sirna Therapeutics Inc.;

(14) An inhibitor of other targets in the HCV life cycle including viral entry, assembly and maturation such as Celgosivir (MBI 3253), a glycoprotein processing inhibitor by Migenix, fusion inhibitor by Trimeris, ACH-0137171 by Achillion;

(15) Immune Modulating Agents.

Receptor agonists such as toll like receptor (;TLR') agonists include ANA245, ANA971, ANA975 (U.S. Pat. Nos. 5,041,426, 4,880,784) by Anadys; CpG-10101a TLR-9 agonist (Coley Pharmaceuticals); an IMPDH inhibitor, mycophenolic acid, a salt or a prodrug thereof sodium mycophenolate or mycophenolate mofetil, or Merimebodib (VX-497, by Vertex); thymosin alpha-1 (Zadaxin or its combination, by SciClone); SCV-07 (SciClone), Belerofon (improved IFN-α by Nautilus); CIVACIR (hepatitis C Immune Globulin) by NABI, or a S1P receptor agonist, e.g. FTY720 or analogue thereof optionally phosphorylated, e.g. as disclosed in EP627406A1, EP778263A1, EP1002792A1, WO02/18395, WO02/76995, WO 02/06268, JP2002316985, WO03/29184, WO03/29205, WO03/62252 and WO03/62248, the disclosures of which are incorporated herein by reference in their entireties; Resiquimod [VML 600] by 3M Pharmaceuticals, an imiquimod analogue that is a potent inducer of interferon-α and other cytokines;

(16) An anti-fibrotic agent, such as a N-phenyl-2-pyrimidine-amine derivative, imatinib (Gleevac), IP-501 by Indevus, and Interferon gamma 1b from InterMune, Pirfenidone (Multiple: TGF Beta agonist, FGF antagonist, PDGF antagonist) by Intermune, Marnac, Shionogi;

(17) Therapeutic vaccines by Intercell (Therapeutic peptide vaccine IC41 HCV), Epimmune/Genecor, Merix, Tripep (Chiron-VacC), immunotherapy (Therapore) by Avant, T cell therapy by CellExSys, monoclonal antibody XTL-002 by STL, ANA 246 and ANA 246 by Anadys, a therapeutic vaccine directed to E2 by Innogenetics, mAb against E2 envelope protein by XTL Bio, GI-5005 (Globelmmune Inc), Inno-Vac-C (WO 9967285, Innogenetics), IC-41 (Intercell), interferon alfa-n3 (Interferon Sciences), Engerix B (SmithKline Beecham);

(18) Other compounds include Ursodiol (EP00269516, Axcan Pharma), HE-2000 (a DHEA analog, Colthurst Ltd), EHC-18 (an immunomodulator, Enzo biochem), histamine dihydrochloride (an H2 agonist, WO09104037, Estero-Anstalt), 1-amino-alkylcyclohexanes (U.S. Pat. No. 6,034,134), alkyl lipids (U.S. Pat. No. 5,922,757), vitamin E and other antitoxidants (U.S. Pat. No. 5,922,757), bile acids (U.S. Pat. No. 5,846,99964), N-(phosphonoacetyl)-L-aspartic acid) U.S. Pat. No. 5,830,905), benzenedicarboxamides (U.S. Pat. No. 5,633,388), polyadenylic acid derivatives (U.S. Pat. No. 5,496,546), 2'3'-dideoxyinosine (U.S. Pat. No. 5,026,687), benzimidazoles (U.S. Pat. No. 5,891,874), plant extracts (U.S. Pat. No. 5,837,257, U.S. Pat. No. 5,725,859 and U.S. Pat. No. 6,056,961) and piperidines (U.S. Pat. No. 5,830, 905); N-(phosphonoacetyl)-L-aspartic acid, benzenedicarboxamides, polyadenylic acid derivatives, glycosylation inhibitors, and nonspecific cytoprotective agents that block cell injury caused by the virus infection;

(19) Any other compound currently in preclinical or clinical development for the treatment of HCV, including Interleukin-10 (Schering-Plough), AMANTADINE (Symmetrel) by Endo Labs Solvay, caspase inhibitor IDN-6556 by Idun Pharma, HCVIMF59 by Chiron, CEPLENE (histamine dichloride) by Maxim, IDN-6556 by Idun PHARM, T67, a beta-tubulin inhibitor by Tularik, FK788 by Fujisawa Healthcare, 1 dB1016 (Siliphos, oral silybin-phosphatidyl choline phytosome), Dication by Immtech, hemopurifier by Aethlon Medical, UT 231B by United Therapeutics; HepeX-C SM1, PPVO-Bay55-8800 (Parapoxvirus ovis) by Bayer; Refanalin (HGF mimetic) by Angion, R803 (Rigel), JTK-003, JTK-002, and JTK-109 (all from Japan Tobacco), HCV-086 (ViroPharma/Wyeth), ISIS-14803 (ISIS Pharmaceuticals), GS-9132 (a polymerase inhibitor by Achillion Pharmaceuticals), HCV-793 (Pharmasset and Roche), R1626 (Roche).

Compounds or drugs in preclinical development can easily be identified by one of skill in the art by searching clinical trial information on the internet, for example, and press release information from respective companies (20) Compounds which increase effectiveness of combination therapy including an antifolate, a 5-fluoropyrimidine (including 5-fluorouracil), a cytidine analogue such as β-L-1,3-dioxolanyl cytidine or β-L-1,3-dioxolanyl 5-fluorocytidine, antimetabolites (including purine antimetabolites, cytarabine, fudarabine, floxuridine, 6-mercaptopurine, methotrexate, and 6-thioguanine), hydroxyurea, mitotic inhibitors (including CPT-11, Etoposide (VP-21), taxol, and vinca alkaloids such as vincristine and vinblastine, an alkylating agent (including but not limited to busulfan, chlorambucil, cyclophosphamide, ifofamide, mechlorethamine, melphalan, and thiotepa), nonclassical alkylating agents, platinum containing compounds, bleomycin, an anti-tumor antibiotic, an anthracycline such as doxorubicin and dannomycin, an anthracenedione, topoisomerase II inhibitors, hormonal agents (including but not limited to corticosteroids (dexamethasone, prednisone, and methylprednisone), androgens such as fluoxymesterone and methyltestosterone, estrogens such as diethylstilbesterol, antiestrogens such as tamoxifen, LHRH analogues such as leuprolide, antiandrogens such as flutamide, aminoglutethimide, megestrol acetate, and medroxyprogesterone), asparaginase, carmustine, lomustine, hexamethyl-melamine, dacarbazine, mitotane, streptozocin, cisplatin, carboplatin, levamasole, and leucovorin. The compounds of the present invention can also be used in combination with enzyme therapy agents and immune system modulators such as interleukin, tumor necrosis factor, macrophage colony-stimulating factor and colony stimulating factor.

Utility of the non-immunosuppressive cyclophilin-binding cyclosporins (hereinafter "cyclosporins of the invention") in treating diseases and conditions as hereinabove specified may be demonstrated in standard animal or clinical tests, e.g. in accordance with the methods described hereinafter.

EXAMPLES

Example 1

In Vitro Assays

Cell culture: HCV replicon cell line, clone A, is obtained from Apath, LLC. The cells are cultured in Dulbecco's modified Eagle's medium (DMEM, Gibco), containing 10% heat-inactivated fetal bovine serum (FBS, Gibco), 2 mM L-glutamine, 1× nonessential amino acids (Gibco), and 1 mg/ml G418 (Invitrogen, Carlsbad, Calif.).

The HCV replicon cell line, Huh-Luc/neo-ET, is obtained from ReBlikon GmbH. The cells are cultured in Dulbecco's modified Eagle's medium (DMEM, Gibco), containing 10% heat-inactivated fetal bovine serum (FBS, Gibco), 2 mM L-glutamine, 1× nonessential amino acids (Gibco), and 0.25 mg/ml G418 (Invitrogen, Carlsbad, Calif.).

QRT-PCR-based HCV replicon assay: To determine antiviral effect of the compounds, HCV replicon cells clone A are treated with compounds serially diluted in DMEM supplemented with 2% FBS and 0.5% DMSO for 48 h, then the total intracellular RNA is extracted, and the level of HCV RNA is determined by real-time quantitative RT-PCR (Taqman) using HCV-specific primers (5'-TCT TCA CGC AGA AAG CGT CTA-3' (Seq. Id No. 1) and 5'-CTG GCA ATT CCG GTG TAC T-3' (Seq Id No. 2) and probe (5'-6-FAM-TCC TGG AGG CTG CAC GAC ACT CAT A-TAMRA-3') (Seq Id No. 3). For each treatment, the quantity of HCV RNA is normalized against the amount of total RNA extracted, which is determined in a Quant-iT assay (Molecular Probe). Each data point represents the average of six replicates in cell culture. $IC_{50}$ is the concentration of the compound at which the HCV RNA level in the replicon cells is reduced by 50%. To monitor cytotoxic effect of the compounds, the viability of the replicon cells following 48 h of compound treatment is determined using a tetrazolium compound (MTS)-based assay (CellTiter 96® AQueous One Solution Cell Proliferation Assay, Promega, Madison, Wis.). $CC_{50}$ is the concentration of the compound at which the cell viability is reduced by 50%.

Luciferase-based HCV replicon assay: In the HCV replicon cell line Huh-Luc/neo-ET, the expression of luciferase is under the control of HCV RNA replication and translation, therefore the antiviral activity can be determined by measuring the reduction of luciferase activity in the cells. HCV replicon cells (Huh-Luc/neo-ET) are treated with compounds serially diluted in DMEM supplemented with 10% FBS and 0.5% DMSO for 48 h. Then the luciferase activity is determined using BrightGlo reagent (Promega) and a LMaxII plate reader (Molecular Probe). The cytotoxicity of the compound is evaluated using the tetrazolium compound (MTS)-based assay described above.

Example 2

Combination Analysis

The effect of drug-drug combination is analyzed using Bliss Independence model, a three-dimensional analytical method developed by Prichard, M. N. and Shipman, C, 1999, Antivir. Res. 14:181-205. In this model, theoretical additive effects are calculated from the dose-response curves of individual compounds using the equation: $Z=X+Y(1-X)$, where X and Y represent the inhibition produced by drug 1 or drug 2 alone, respectively, and Z represents the effect produced by the combination of drug 1 and drug 2. The theoretical additive surface is subtracted from the actual experimental surface, resulting in a surface which would appear as a horizontal plane at 0% inhibition if the combination was merely additive. The 95% confidence intervals for the experimental dose-response surface are used to evaluate the data statistically.

Analysis of the effect of combination treatment, are examined using nine-day viral RNA reduction assays. HCV replicon cells clone A are treated with compounds in DMEM supplemented with 10% FBS and 0.2% DMSO for 3, 6, or 9 days, then the total intracellular RNA is extracted, and the level of HCV RNA is determined by real-time quantitative RT-PCR (Taqman) using HCV-specific primers and probe as described above. For each treatment, the quantity of HCV RNA is normalized against the amount of total RNA extracted, which is determined in a Quant-iT assay (Molecular Probe). The log reduction of HCV RNA is calculated by comparing the level of HCV RNA in compound-treated cells to that of untreated cells.

Figure 1:
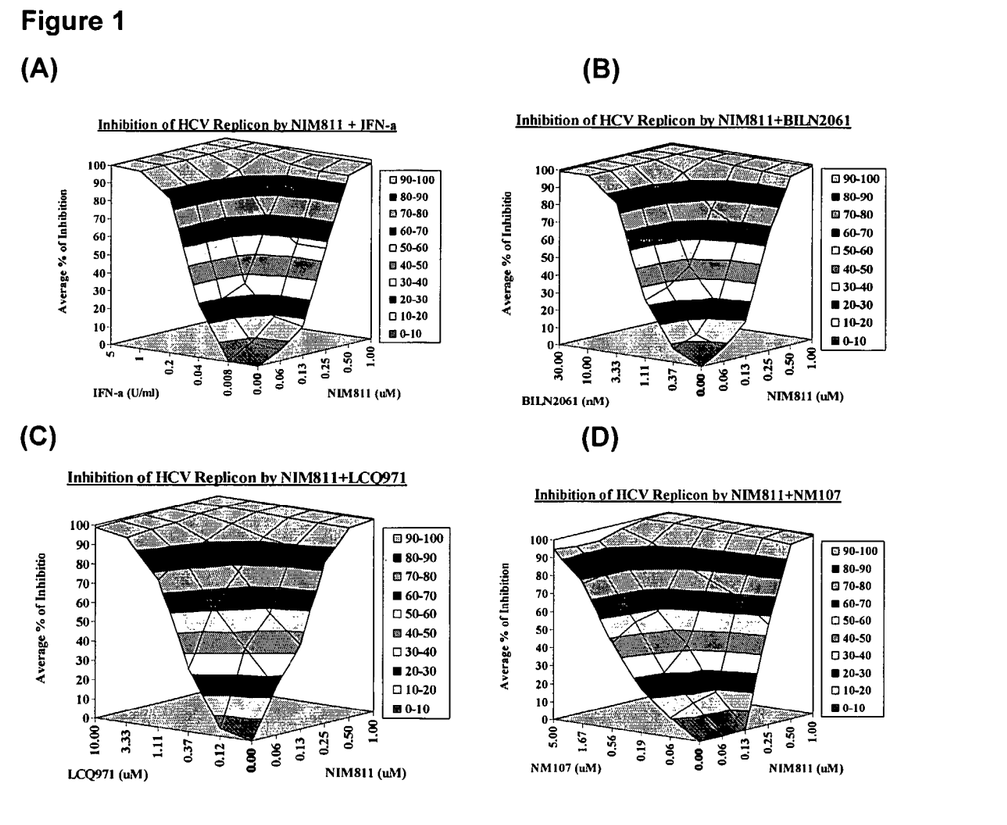
FIG. 1 illustrates the effect of combination treatment using the cyclosporin of the invention (NIM811) and (A) interferon-α, (B) BILN2061, (C) LCQ971 or (D) NM107

The effect of the combination of NIM811 ([MeIle]$^4$-cyclosporin) with IFN-α is examined using the assay system and the mathematic model described above. The HCV replicon cells are treated with various concentrations of NIM811 and IFN-α either alone or in combination for 48 h. As shown in FIG. 1A, there is a stronger inhibition of HCV with the combination in a concentration-dependent manner. Importantly, there is no significant increase of cytotoxicity using the combination at the concentrations tested.

In another embodiment, BILN2061 is a specific inhibitor of HCV NS3-4A serine protease (Lamarre D, et al. 2003. Nature 426:186). The effect of the combination of NIM811 with BILN2061 is examined using the assay system and the mathematic model described above. The HCV replicon cells are treated with various concentrations of NIM811 and BILN2061 either alone or in combination for 48 h. As shown in FIG. 1B there is a stronger inhibition of HCV with the combination in a concentration-dependent manner. Importantly, there is no significant increase of cytotoxicity with the combination at the concentrations tested.

LCQ971 is a non-nucleoside inhibitor of HCV NS5B RNA-dependent RNA polymerase (WO-00185172, WO-02098424, WO-03059356, Dhanak D. et al. 2002. J. Biol. Chem. 277:38322-7). The effect of the combination of NIM811 with LCQ971 is examined in the replicon system, in which the cells are treated with various concentrations of NIM811 and LCQ971 either alone or in combination for 48 h. As shown in FIG. 1C, there is a further inhibition of HCV in a concentration-dependent manner when the two agents are used in combination. The effect of the combination is determined to be synergistic as analyzed using the Bliss Independence model. Importantly, there is no significant increase of cytotoxicity with the combination at the concentrations tested.

NM107, a nucleoside analogue, is a specific inhibitor of HCV NS5B RNA-dependent RNA polymerase. NM107 is the active metabolite of NM283, an experimental drug currently in Phase II clinical trial for treating hepatitis C. The effect of the combination of NIM811 with NM107 is also examined in the replicon system, in which the cells are treated with various concentrations of NIM811 and NM107 either alone or in combination for 48 h. As shown in FIG. 1D, there is a further inhibition of HCV in a concentration-dependent manner when the two agents are used in combination. The effect of the combination is synergistic as analyzed using the Bliss Independence model. Importantly, there is no significant increase of cytotoxicity with the combination at the concentrations tested.

Figure 2:
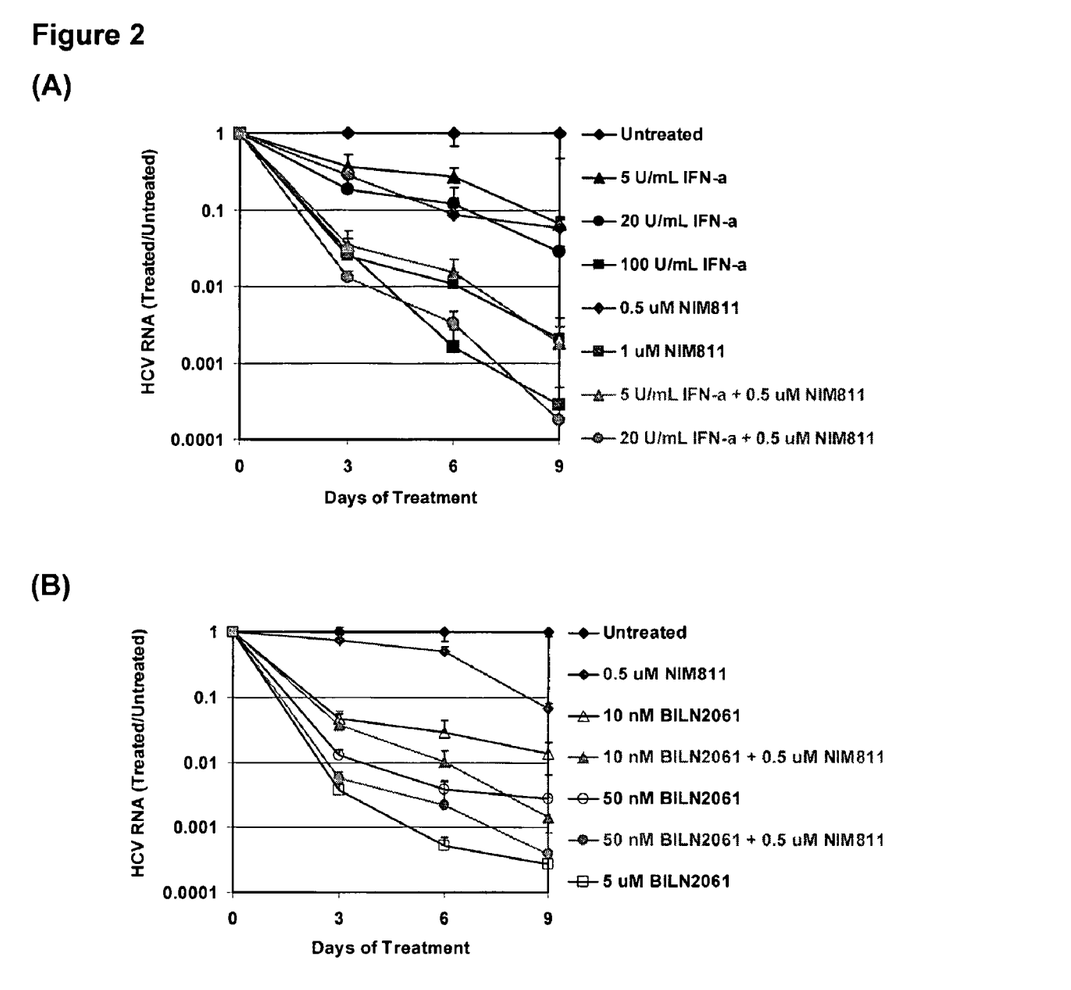
FIG. 2 illustrates a comparison of the reduction of cell replication with treatment of NIM811 alone or in combination with (A) interferon-α or (B) BILN2061.

As shown in FIG. 2, 0.5 μM NIM811 results in 1.2-log reduction of HCV RNA in the replicon cells after 9 days of treatment, while 1 μM NIM811 results in a greater than 3-log viral RNA reduction. Importantly, the combination of 0.5 μM NIM811 and 5 U/ml IFN-α lead to a 2.7-log reduction of HCV RNA, which is significantly better than that of 0.5 μM NIM811 alone or 5 U/ml IFN-α alone (1.2-log). Moreover, the combination of 0.5 μM NIM811 and 20 U/ml IFN-α leads to a 3.7-log reduction of HCV RNA, which is greater than that of much higher concentrations of IFN-α alone or NIM811 alone.

Similarly, as shown in FIG. 2B, the combinations of NIM811 and BILN2061, a specific inhibitor of HCV NS3-4A protease, result in greater viral RNA reductions than those of much higher concentrations of BILN2061 alone or NIM811 alone.

Example 3

Resistance Frequency Analysis

Figure 3:
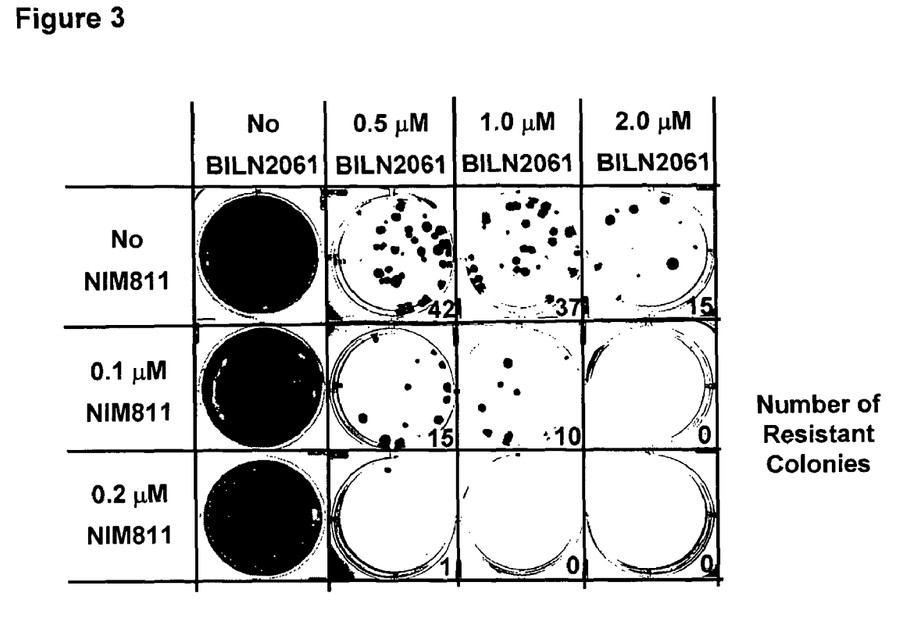
FIG. 3 illustrates the inhibitory effect of a combination of NIM811 and BILN2061 on viral RNA.

HCV replicon cells clone A are treated with various concentrations of NIM811 and BILN2061 either alone or in combination in the presence of 1 mg/ml G418. Resistant colonies start to form after treating the cells with BILN2061 for 2 weeks. Cell cultures collected after 3 weeks of treatment are shown in FIG. 3. The numbers of resistant colonies are also shown. There is a drastic reduction of resistance rate with the combination of NIM811 and BILN2061 than either compound alone. This data suggests that the combination therapy would help to suppress the emergence of resistance.

Example 4

Clinical Trials

As a proof-of-concept study, a total of 15~30 patients with hepatitis C viral infection are enrolled in a study of 2~12 weeks. Each patient receives orally a compound of formula I, e.g. [Melle]$^4$-cyclosporin at a dose of 0.5 to 20 mg/kg/day either alone or in combination with co-agents, such as pegylated IFN-α at a standard dose. The pre- and post-treatment serum levels of hepatitis C virus are determined for each patient. The cyclosporins of the invention may be administered as the sole ingredient or in combination or alteration with other antiviral agents, especially agents active against HCV. In combination therapy, effective dosages of two or more agents are administered together, whereas in alternation or sequential-step therapy, an effective dosage of each agent is administered serially or sequentially. In general, combination therapy is typically preferred over alternation therapy because it induces multiple simultaneous stresses on the virus. The dosages given will depend on absorption, inactivation and excretion rate of the drug as well as other factors. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. The efficacy of a drug against the viral infection can be prolonged, augmented, or restored by administering the compound in combination or alternation with a second, and perhaps third antiviral compound that induces a different gene mutation than that caused by the principle drug in a drug resistant virus. Alternatively, the pharmacokinetic, biodistribution or other parameters of the drug can be altered by such combination or alternation therapy.

Daily dosages required in practicing the method of the present invention will vary depending upon, for example, the non-immunosuppressive cyclophilin-binding cyclosporin employed, the host, the mode of administration, the severity of the condition to be treated. Suitable daily dosages of [Melle]$^4$-cyclosporin for patients are on the order of from e.g. 0.5 to 20 mg/kg (p.o or i.v.), preferably 25-75 mg/day, 75-200 mg/day, most preferably 200-400 mg/together with one or more pharmaceutically acceptable diluents or carriers. The amount of co-agent in the dosage form can vary greatly, e.g., 0.00001 to 1000 mg/kg active ingredient.

Daily dosages with respect to the co-agent used will vary depending upon, for example, the compound employed, the host, the mode of administration and the severity of the condition to be treated. For example, the pegylated interferon may be administered parenterally one to three times per week, such as once a week, at a total weekly dose ranging from 2 to 10 million IU, or 5 to 10 million IU, or 8 to 10 million IU. Because of the diverse types of co-agent that may be used, the amounts can vary greatly, e.g., 0.0001 to 5,000 mg/kg per day.

The current standard of care for treating hepatitis C is the combination of pegylated interferon alpha with ribavirin, of which the recommended doses include 1.5 μg/kg/wk peginterferon alfa-2b or 180 μg/wk peginterferon alfa-2a, plus 1,000 to 1,200 mg daily of ribavirin for 48 weeks for genotype I patients, or 800 mg daily of ribavirin for 24 weeks for genotype ⅔ patients.

The cyclosporins of the invention may be administered by any conventional route, in particular enterally, e.g. orally, for example in the form of solutions for drinking, tablets or capsules or parenterally, for example in the form of injectable solutions or suspensions. Preferred pharmaceutical compositions may be e.g. those based on microemulsions as described in UK 2,222,770 A.

In accordance with the foregoing the present invention provides in a yet further aspect:

4. A pharmaceutical combination comprising a) a first agent which is a non-immunosuppressive cyclophilin-binding cyclosporin, e.g. a compound of formula I, and b) a co-agent, e.g. one or more co-agents as defined above.

5. A method as defined above comprising co-administration, e.g. concomitantly or in sequence, of a therapeutically effective amount of a non-immunosuppressive cyclophilin-binding cyclosporin, e.g. a compound of formula I, and a co-agent, e.g. one or more co-agents as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic or additive therapeutic effect, compared to a monotherapy applying only one of its pharmaceutically active ingredients. An example of a synergistic combination is a combination of a non-immunosuppressive cyclophilin-binding cyclosporin with IFN-α.

[Melle]$^4$-cyclosporin (NIM811) is an example of a suitable non-immunosuppressive cyclophilin-binding cyclosporin for use according to the invention.

What is claimed is:

1. A pharmaceutical composition comprising a non-immunosuppressive cyclophilin-binding cyclosporin and an inhibitor of HCV NS5B polymerase.

2. The composition of claim 1 wherein the non-immunosuppressive cyclophilin-binding cyclosporin is of formula I in which
W is MeBmt, dihydro-MeBmt or 8'-hydroxy-MeBmt;
X is αAbu, Val, Thr, Nva or O-methyl threonine (MeOThr);
R is Sar, (D)-MeSer, (D)-MeAla, or (D)-MeSer(Oacetyl);
Y is MeLeu, γ-hydroxy-MeLeu, MeIle, MeVal, MeThr, MeAla,
  MeaIle, MeaThr, N-ethylVal, N-ethylIle, N-ethylThr, N-ethylPhe, N-ethylTyr or N-ethylThr(Oacetyl);
Z is Val, Leu, MeVal or MeLeu; and
Q is MeLeu, γ-hydroxy-MeLeu or MeAla.

3. The composition of claim 2, wherein the inhibitor of HCV NS5B polymerase is a 2'-C-methyl ribofuranosyl cytidine or its prodrug.

4. A method comprising co-administration of a therapeutically effective amount of a non-immunosuppressive cyclophilin-binding cyclosporin and an inhibitor of HCV NS5B polymerase.

5. The method of claim 4 wherein the non-immunosuppressive cyclophilin-binding cyclosporin is of formula I in which
W is MeBmt, dihydro-MeBmt or 8'-hydroxy-MeBmt;
X is αAbu, Val, Thr, Nva or O-methyl threonine (MeOThr);
R is Sar, (D)-MeSer, (D)-MeAla, or (D)-MeSer(Oacetyl);
Y is MeLeu, γ-hydroxy-MeLeu, MeIle, MeVal, MeThr, MeAla,
  MeaIle, MeaThr, N-ethylVal, N-ethylIle, N-ethylThr, N-ethylPhe, N-ethylTyr or N-ethylThr(Oacetyl);
Z is Val, Leu, MeVal or MeLeu; and
Q is MeLeu, γ-hydroxy-MeLeu or MeAla.

6. The method of claim 5, wherein the inhibitor of HCV NS5B polymerase is a 2'-C-methyl ribofuranosyl cytidine or its prodrug.

7. A pharmaceutical composition comprising a non-immunosuppressive cyclophilin-binding cyclosporin and an inhibitor of HCV NS5B polymerase, with the proviso that said inhibitor of HCV NS5B polymerase is not NM283.

8. The composition of claim 7 wherein the non-immunosuppressive cyclophilin-binding cyclosporin is of formula I in which
W is MeBmt, dihydro-MeBmt or 8'-hydroxy-MeBmt;
X is αAbu, Val, Thr, Nva or O-methyl threonine (MeOThr);
R is Sar, (D)-MeSer, (D)-MeAla, or (D)-MeSer(Oacetyl);
Y is MeLeu, γ-hydroxy-MeLeu, MeIle, MeVal, MeThr, MeAla,
  MeaIle, MeaThr, N-ethylVal, N-ethylIle, N-ethylThr, N-ethylPhe, N-ethylTyr or N-ethylThr(Oacetyl);
Z is Val, Leu, MeVal or MeLeu; and
Q is MeLeu, γ-hydroxy-MeLeu or MeAla.

9. The composition of claim 7 wherein the non-immunosuppressive cyclophilin-binding cyclosporin is [MeIle][4]-cyclosporin.

10. A method comprising co-administration of a therapeutically effective amount of a non-immunosuppressive cyclophilin-binding cyclosporin and an inhibitor of HCV NS5B polymerase, with the proviso that said inhibitor of HCV NS5B polymerase is not NM283.

11. The method of claim 10 wherein the non-immunosuppressive cyclophilin-binding cyclosporin is of formula I

I in which

W is MeBmt, dihydro-MeBmt or 8'-hydroxy-MeBmt;
X is αAbu, Val, Thr, Nva or O-methyl threonine (MeOThr);
R is Sar, (D)-MeSer, (D)-MeAla, or (D)-MeSer(Oacetyl);
Y is MeLeu, γ-hydroxy-MeLeu, MeIle, MeVal, MeThr, MeAla, MeaIle, MeaThr, N-ethylVal, N-ethylIle, N-ethylThr, N-ethylPhe, N-ethylTyr or N-ethylThr(Oacetyl);
Z is Val, Leu, MeVal or MeLeu; and
Q is MeLeu, γ-hydroxy-MeLeu or MeAla.

12. The method of claim 11 wherein the non-immunosuppressive cyclophilin-binding cyclosporin is [MeIle]$^4$-cyclosporin.

* * * * *